(12) United States Patent
Zribi et al.

(10) Patent No.: US 7,627,357 B2
(45) Date of Patent: Dec. 1, 2009

(54) SYSTEM AND METHOD FOR NON-INVASIVE GLUCOSE MONITORING

(75) Inventors: Anis Zribi, Rexford, NY (US); Peter Joseph Codella, Niskayuna, NY (US); Min-Yi Shih, Niskayuna, NY (US); Ganesh Chandan Gangadharan, Bangalore (IN); Rui Chen, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 706 days.

(21) Appl. No.: 11/172,648

(22) Filed: Jun. 30, 2005

(65) Prior Publication Data

US 2007/0004975 A1 Jan. 4, 2007

(51) Int. Cl.
*A61B 5/1455* (2006.01)
(52) U.S. Cl. ...................... 600/319; 600/310
(58) Field of Classification Search .............. 600/309, 600/310, 316, 317, 318, 319, 322
See application file for complete search history.

(56) References Cited

U.S. PATENT DOCUMENTS

| | | | | |
|---|---|---|---|---|
| 4,014,321 A | * | 3/1977 | March | 600/319 |
| 5,687,721 A | * | 11/1997 | Kuhls | 600/316 |
| 5,882,301 A | * | 3/1999 | Yoshida | 600/318 |
| 5,961,449 A | * | 10/1999 | Toida et al. | 600/319 |
| 6,064,897 A | * | 5/2000 | Lindberg et al. | 600/316 |
| 6,442,410 B1 | | 8/2002 | Steffes | |
| 6,485,703 B1 | * | 11/2002 | Cote et al. | 424/9.1 |
| 6,574,490 B2 | | 6/2003 | Abbink et al. | 600/316 |
| 6,630,673 B2 | * | 10/2003 | Khalil et al. | 250/341.8 |
| 7,215,984 B2 | * | 5/2007 | Diab et al. | 600/310 |
| 7,302,284 B2 | * | 11/2007 | Baker et al. | 600/323 |
| 2004/0138539 A1 | | 7/2004 | Jay | |
| 2004/0260158 A1 | | 12/2004 | Hogan | 600/316 |
| 2005/0030540 A1 | * | 2/2005 | Thornton | 356/432 |

FOREIGN PATENT DOCUMENTS

| | | |
|---|---|---|
| EP | 1205753 | 5/2002 |
| WO | WO 2006009969 | 1/2006 |

OTHER PUBLICATIONS

Wang et al., Analysis of Metabolites in Aqueous Solution . . . , Feb. 20, 1993, Applied Optics, vol. 32, No. 6, 925-929.*
Robert W. Knighton, Xiang-Run Huang, "Linear Birefringence of the Central Human Cornea", Investigative Ophthalmology & Visual Science, Jan. 2002, vol. 43, No. 1, pp. 82-86.
European Patent Office, Extended European Search Report, 9 pages, dated May 22, 2007.

* cited by examiner

*Primary Examiner*—Eric F Winakur
(74) *Attorney, Agent, or Firm*—Scott J. Asmus

(57) ABSTRACT

A method for determining analyte concentration levels is provided. The method includes acquiring radiation scattered off or transmitted by a target, analyzing at least a first portion of the radiation via a first technique to generate a first measurement of analyte concentration levels, and analyzing at least a second portion of the radiation via a second technique to generate a second measurement of analyte concentration levels. The method further determines analyte concentration levels based on at least one of the first measurement or the second measurement. In addition, a system for implementing the method and a probe for measuring and monitoring the analyte concentration levels is provided.

21 Claims, 4 Drawing Sheets

SYSTEM AND METHOD FOR NON-INVASIVE GLUCOSE MONITORING

BACKGROUND

The invention relates generally to medical monitoring systems, and more particularly to a non-invasive glucose monitoring system and method.

Certain conditions in diabetics lead to insufficient production of insulin, or render the cells incapable of recognizing or detecting the insulin produced. Moreover, this may lead to the person experiencing improper regulation of insulin produced by their body. In any of these conditions, it may be desirable to acquire information about the glucose level in blood of the person so that measures may be taken to prevent further deterioration of the condition.

Most glucose monitoring techniques have been predominantly invasive. For example, glucose monitoring using blood usually requires extraction of blood from the body of the subject. Although urine glucose monitoring is non-invasive, the presence of glucose in the urine typically does not accurately reflect how high or low the blood glucose concentration is. Furthermore, urine glucose measurements lag behind the blood glucose concentration by about 20 to 30 minutes, making it practically unusable for detecting surges in blood glucose levels.

Attempts have been made to monitor glucose non-invasively by utilizing near-infrared spectroscopy on the skin of the subject. These techniques rely on the scattered, absorbed or transmitted radiation to determine glucose levels. However, the variables associated with the skin (such as thickness, texture, and so forth) contribute to the variable reflection and refraction of light, thereby preventing accurate and reliable non-invasive measurement of blood glucose concentration. Furthermore, skin also causes large specular reflectance, further contributing to these problems. Similarly, changes in skin texture or temperature over time may also alter the measurement readings. In addition, the presence of multiple analytes, like water, that absorb in the near-infrared region confound the measurements and make it difficult to produce a reliable signal from the skin.

Thus, there is a need for a system and method to make effective measurements of analytes, such as glucose levels, in human tissue in a non-invasive manner.

SUMMARY

According to one aspect of the present technique, a method for determining analyte concentration levels is provided. The method includes acquiring radiation scattered off or transmitted by a target, analyzing at least a first portion of the radiation via a first technique to generate a first measurement of analyte concentration levels, and analyzing at least a second portion of the radiation via a second technique to generate a second measurement of analyte concentration levels. The method further determines analyte concentration levels based on at least one of the first measurement or the second measurement.

In accordance with another aspect of the present technique, a system for measuring an analyte concentration is provided. The system includes a filter for separating scattered radiation into a first portion and a second portion. A spectrometer processes the first portion to generate a first measurement of an analyte concentration levels. A polarimeter processes the second portion to generate a second measurement of an analyte concentration levels. An analysis component generates analyte concentration levels based upon the first measurement and the second measurement.

In accordance with another aspect of the present technique, a tangible media is provided, which includes a routine that generates a measurement of analyte concentration levels based upon a spectroscopic measurement of analytes and a polarimetric measurement of the analyte concentration levels.

These and other advantages and features will be more readily understood from the following detailed description of preferred embodiments of the invention that is provided in connection with the accompanying drawings.

DETAILED DESCRIPTION OF EXEMPLARY EMBODIMENTS

In the subsequent paragraphs, an approach for non-invasively measuring the concentration of analytes, i.e., substances or compounds undergoing analysis, in human tissue, will be explained in detail. The approach described hereinafter describes measurement of glucose content in human tissue non-invasively, and may be applicable for monitoring blood glucose levels in diabetics or for other clinical or diagnostic uses. As will be appreciated by those of ordinary skill in the art, the present technique is applicable to other analytes besides glucose and may be useful in diagnostic or clinical contexts other than the monitoring or measurement of blood glucose concentration. Indeed, the exemplary uses and implementations described herein are merely provided as examples to facilitate understanding of the presently contemplated techniques. Therefore, the various aspects of the present technique will be explained, by way of example only, with the aid of figures hereinafter.

Figure 1:
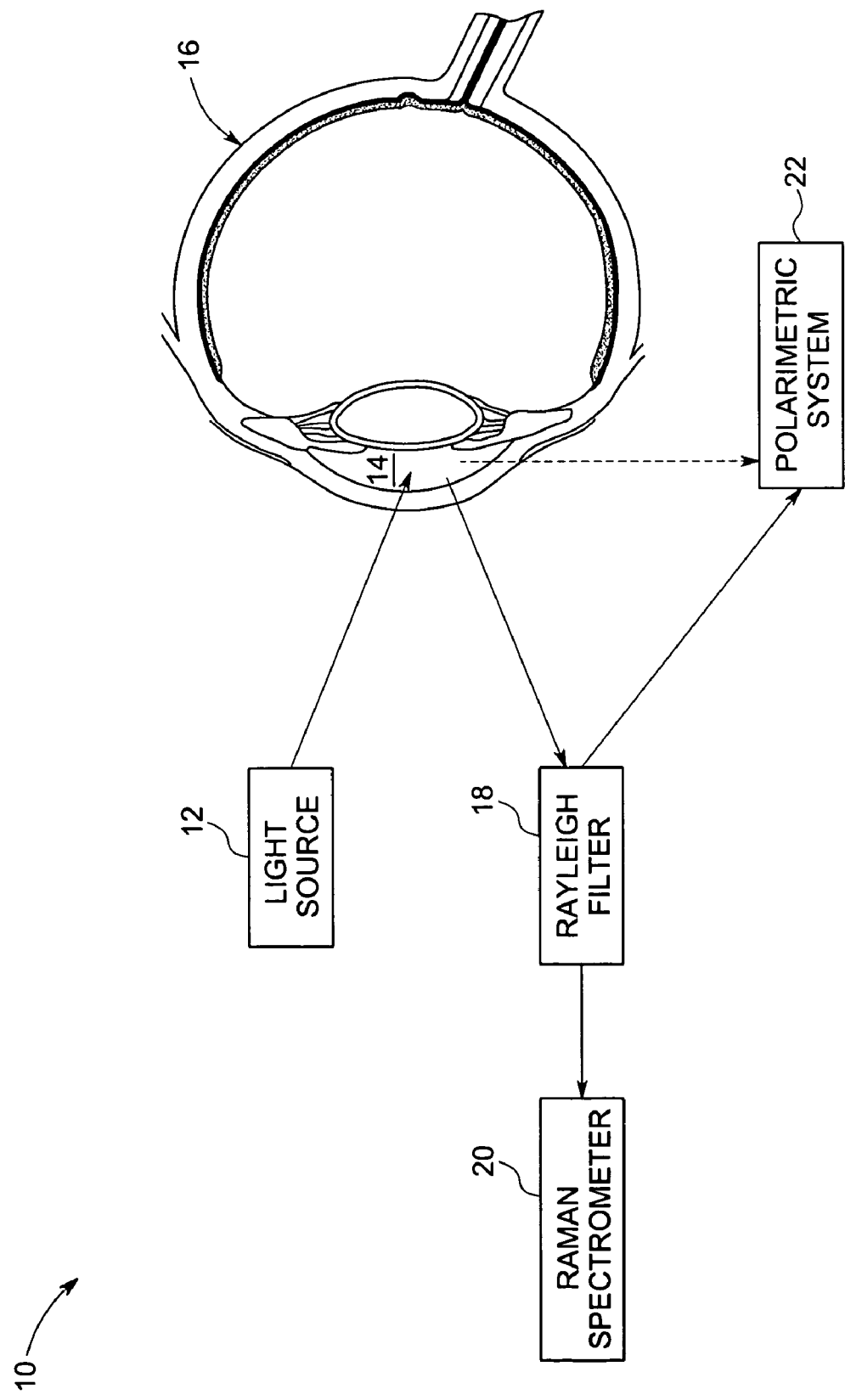
FIG. 1 is a diagrammatic representation of an exemplary glucose monitoring system for use in accordance with the present technique.

Referring generally to FIG. 1, an analyte concentration measurement system will be described by reference to an exemplary glucose monitoring system designated generally by numeral 10. It should be appreciated; however, that the analyte concentration measurement system may find application in a range of settings and systems, and that its use in the glucose monitoring system shown is but one such application.

The glucose monitoring system 10 includes a light source 12, which in one embodiment includes a laser source. The light source 12 provides a beam of coherent photons, whose angle of polarization may be controlled at the light source 12 during or after transmission. In the depicted embodiment, the beam of coherent photons is incident on the aqueous humor 14 of the eye 16 of a subject. The molecules in the aqueous humor 14 are enantiomers, which exhibit chirality. This property of the aqueous humor 14 alters the angle of polarization in the scattered beam of coherent photons. In addition, light scattered from molecules have frequency shift signatures corresponding to molecular structure. In the present embodiment, Raman spectroscopy technique is utilized to detect the shift in wavelength in the beam of coherent photons and polarimetry is utilized to detect the shift in polarization.

In the depicted embodiment, a Rayleigh filter 18 is used to filter the Raman signals from other scattered photons, such as those associated with Rayleigh and Brioullin scattering. The filtered Raman signals are transmitted through the filter 18 to a Raman spectrometer 20 for analysis, while the other scattered photons are reflected off the Rayleigh filter 18 and directed to a polarimetric system 22 for analysis. The polarimetric system 22 may, however, also receive scattered rays reflected from the aqueous humor 14 directly. Both the Raman spectrometer 20 and the polarimetric system 22 provide concentrations of one or more analytes, such as glucose, ascorbate, and albumin, from the respective photons directed to them. In one embodiment, the respective measurements of the Raman and polarimetric system are combined together to produce a final measurement of the one or more analyte concentrations.

Figure 2:
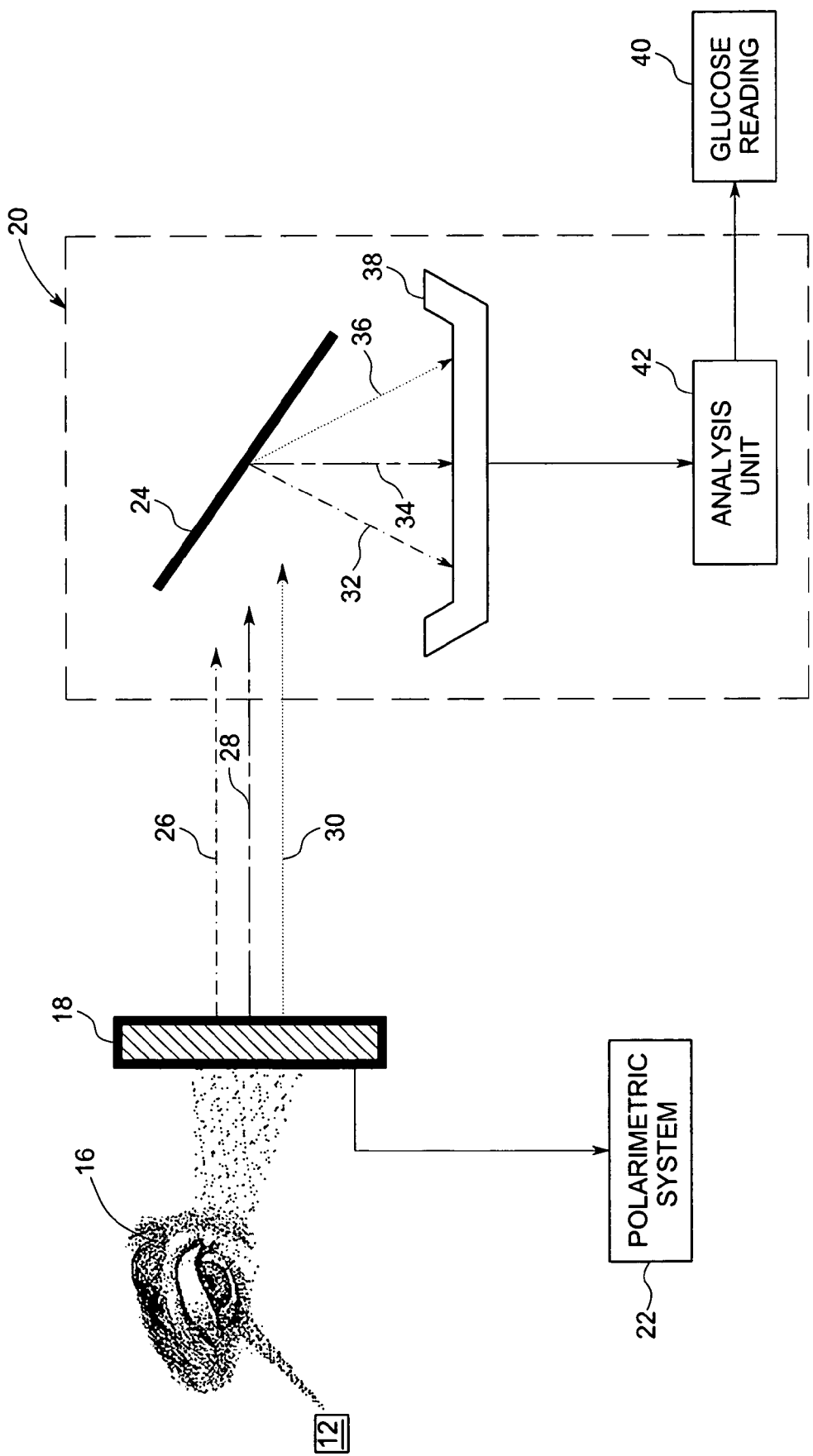
FIG. 2 is a diagrammatic representation of a Raman spectroscopy system for estimating glucose level of a subject in accordance with aspects of the present technique.

Referring now to FIG. 2, a Raman spectroscopy system 20 for estimating analyte concentration in a subject is shown. As will be appreciated by those of ordinary skill in the art, spectroscopy facilitates measurement of light intensity as a function of wavelength, i.e., a spectrum. In a spectroscopic measurement, the Rayleigh filter 18 functions as a notch filter, so that photons within a desired range of wavelengths are transmitted through the filter 18 while photons outside the desired range of wavelengths are not transmitted. The range of wavelengths transmitted depends on the illumination wavelength. Typically, a Rayleigh or other similar filters transmit wavelengths between 100 and 4000 wave-numbers longer than the excitation wavelength. Further, the Rayleigh filter 18 allows only signals useful for Raman spectroscopy to pass through the filter 18. In other words, the Rayleigh filter 18 removes light scattered having a wavelength corresponding to the excitation wavelength, while allowing the rest of the wavelengths to pass through. Thus, spectroscopic measurement may be performed via a spectrometer, such as a diffraction grating, a Fabry-Perot filter, an interferometric filter, and the like. In the depicted embodiment, the Raman signals are indicative of the glucose concentration.

As illustrated, the light source 12 emits light rays toward the aqueous humor 14 of the eye. A small portion of this light interacts with molecules such as glucose in the humor. Such interactions produce scattered light. While most of the light is scattered without a change in wavelength, some of the photons interact with molecular species resulting in a transfer of energy between the molecule and the photon. This energy transfer causes a wavelength shift in the scattered light. Photons exhibiting these shifts are called "Raman" scattered photons, the measurement of which is termed Raman spectroscopy. Since Raman scattering originates in molecular-photon interactions, Raman spectroscopy yields spectra that are characteristic for particular molecules. Raman scattering is a relatively low probability process. Therefore, high intensity light sources, such as lasers are normally used for illumination. A tunable laser may be used to achieve resonant conditions (i.e., when the excitation energy (wavelength) is coincident with a molecular absorption.) In this case, the Raman scattering may be increased by as much as $10^4$. Such an increase allows reduction of incident laser intensity to achieve equivalent spontaneous Raman scattering during measurements, in one embodiment.

Glucose is one of the molecular species in the aqueous humor 14 of the eye 16 that exhibits Raman scattering. The intensity of wavelength-shifted light from the aqueous humor 14 of the eye 16 is altered based on the glucose concentration in the aqueous humor. Therefore, by detecting and measuring the intensity of the scattered light the glucose concentration can be deduced. As will be appreciated by those of ordinary skill in the art, albumin, ascorbate, lactate, and urea are also Raman-active molecules that may be present in the aqueous humor 14. Ascorbate and albumin concentrations do not vary as much as those of glucose. Expected concentrations of albumin in the aqueous humor 14 are higher than those of glucose. Whereas the Raman signatures of these molecules are different from each other, their respective concentrations can be determined by measuring the area under the respective peaks they produce or analyzing the data with one of the numerous mathematical data analysis algorithms, such as principle component analysis.

The reflected light is filtered by the Rayleigh filter 18 and the transmitted photons are made incident on a diffraction grating 24, which separates the different wavelengths of light. In other embodiments, photons may be made incident on other spectrographs, such as a holographic filter or an interferometer. As shown, when light rays of different wavelengths 26, 28, and 30 fall on the diffraction grating 24, these are spatially separated as rays 32, 34, and 36 respectively. This diffraction of the light rays depends on the line spacing of the diffraction grating or on other characteristics of the respective spectroscopic device. Therefore, as will be appreciated by those of ordinary skill in the art, the spectroscopic device may be selected based on the desired spatial separation of the different wavelengths on a detector. In the depicted embodiment, the different wavelengths of light rays are detected by a detector 38, which detects the intensities of light rays at those wavelengths. The detector 38 converts the detected intensities for the respective wavelengths into an electrical signal. The electrical signal may be processed to determine a glucose (or other analyte) concentration 40 by analysis of the signal in an analysis unit 42. This may be performed on the fly or the glucose concentration may be determined utilizing a look-up table within the analysis unit 42.

Figure 3:
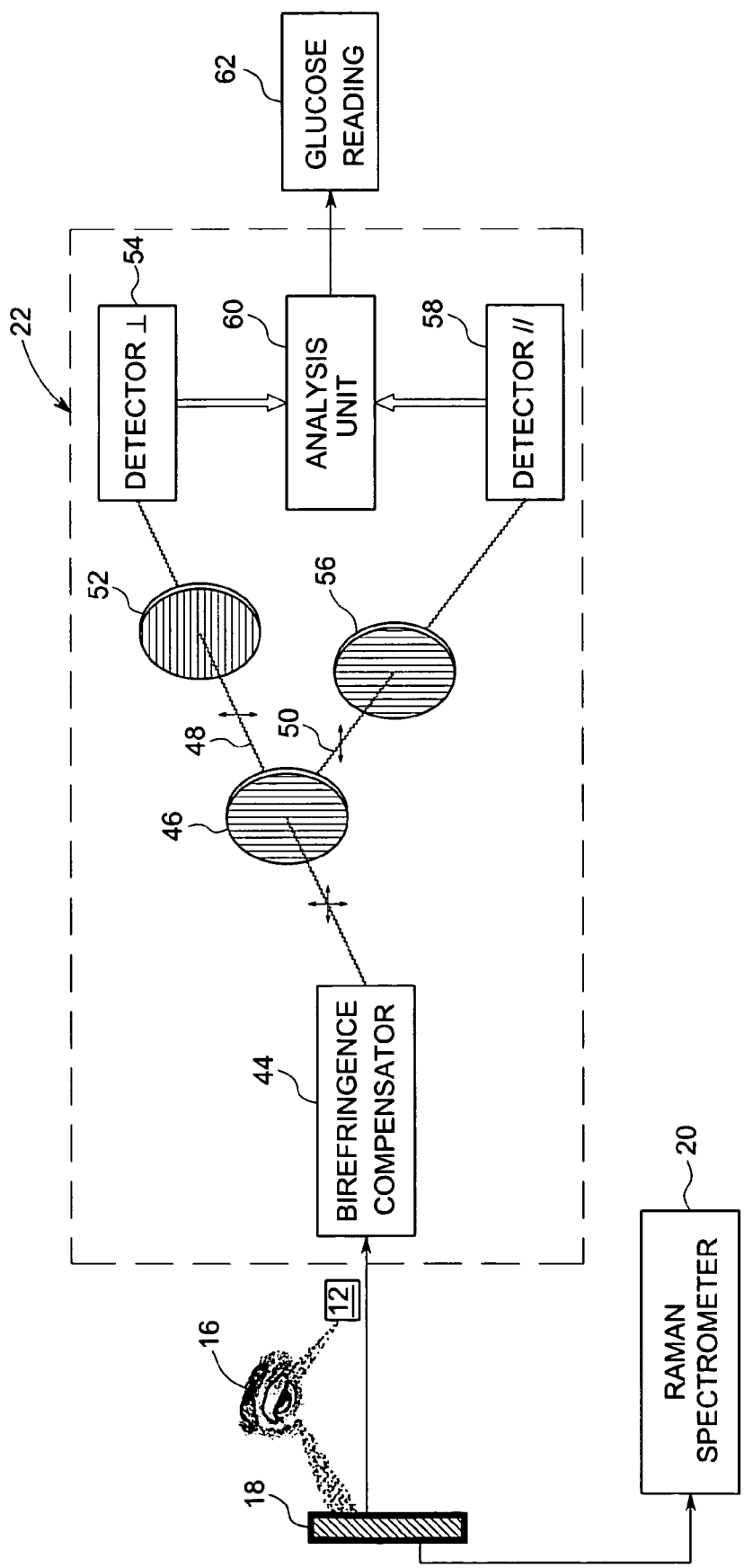
FIG. 3 is a diagrammatic representation of a polarimetry system for estimating glucose level of a subject in accordance with aspects of the present technique.

Turning now to FIG. 3, a polarimetry system 22 for estimating analyte concentration level in a subject is illustrated. As previously described, in one embodiment, photons not transmitted by the Rayleigh filter 18 are fed into the polarimetry system 22 for analysis. In other embodiments, the polarimetry system 22 may receive photons scattered directly by the eye in addition to or instead of those not transmitted by the filter 18. The polarimetry system 22 analyzes the shift in polarization of the scattered photons, which may be used to determine analyte (such as glucose) concentration.

In addition, as will be appreciated by those of ordinary skill in the art, the cornea of the eye 16 exhibits a birefringence property. In other words, a ray of light is split into two parallel rays that are polarized perpendicularly. This birefringence effect produces multiple refractive indices along different axes, causing different light rays originating from different locations in the eye 16 to refract differently. Therefore, in the depicted embodiment, a birefringence compensator 44 is utilized to correct for the birefringence effect, making the light rays location independent.

The birefringence-corrected light rays from the birefringence compensator 44 are polarized at a particular axis. These light rays may be polarized linearly or circularly. A beam splitter 46 may be utilized to split the light beam into perpendicular-polarized beams 48 and parallel-polarized beams 50. The perpendicular-polarized beams 48 are fed into an analyzer (or a polarized light filter) 52, and then into a detector 54. The detector 54 detects the perpendicular-polarized beam 48 and converts the perpendicular-polarized beam 48 of light into an electrical signal. Similarly, the parallel-polarized beam 50 is fed into another analyzer 56, and then into a second detector 58. Detector 58 detects the parallel-polarized beam 50 and converts the same into an electrical signal. Detectors 54 and 58 may include amorphous silicon detectors, indium gallium arsenide (InGaAs) detectors, or the like. Detectors 54 and 58 may be chosen based on the wavelength of light that is to be detected. For example, an InGaAs detector may be utilized for detection of light in the near-infrared portion of the spectrum. The electrical signals from detectors 54 and 58 are fed into an analysis unit 60, which converts the same into analyte concentration 62 via the following equation:

$$a_{total} = L(a_{albumin} * C_{albumin} + a_{ascorbate} * C_{ascorbate} + a_{glucose} * C_{glucose});$$

where, $a_i$ is the specific rotation for each analyte; L is the optical path length over which light molecule-interaction occurs; $C_i$ is the concentration of the optically active analytes; and $a_{total}$ is the observed rotation. Thus, the albumin concentration ($C_{albumin}$), ascorbate concentration ($C_{ascorbate}$), and glucose concentration ($C_{glucose}$) are provided by the polarimetric measurement, as a weighted summation of the three.

The computation of the analyte concentration 62 may be performed on the fly within the analysis unit 60 or may be looked-up against pre-computed analyte concentration levels. Because albumin, ascorbate and glucose levels are the main chiral components of the aqueous humor, the analyte concentration 62 may include albumin concentration, ascorbate concentration, and/or glucose concentration levels. The polarimetric signatures of albumin, ascorbate and glucose are indistinguishable, because they are represented as the weighted sum of the three. Furthermore, one or both of the analysis units 42 and 60 may be built into one or more microelectro-mechanical systems (MEMS) based integrated chip.

Figure 4:
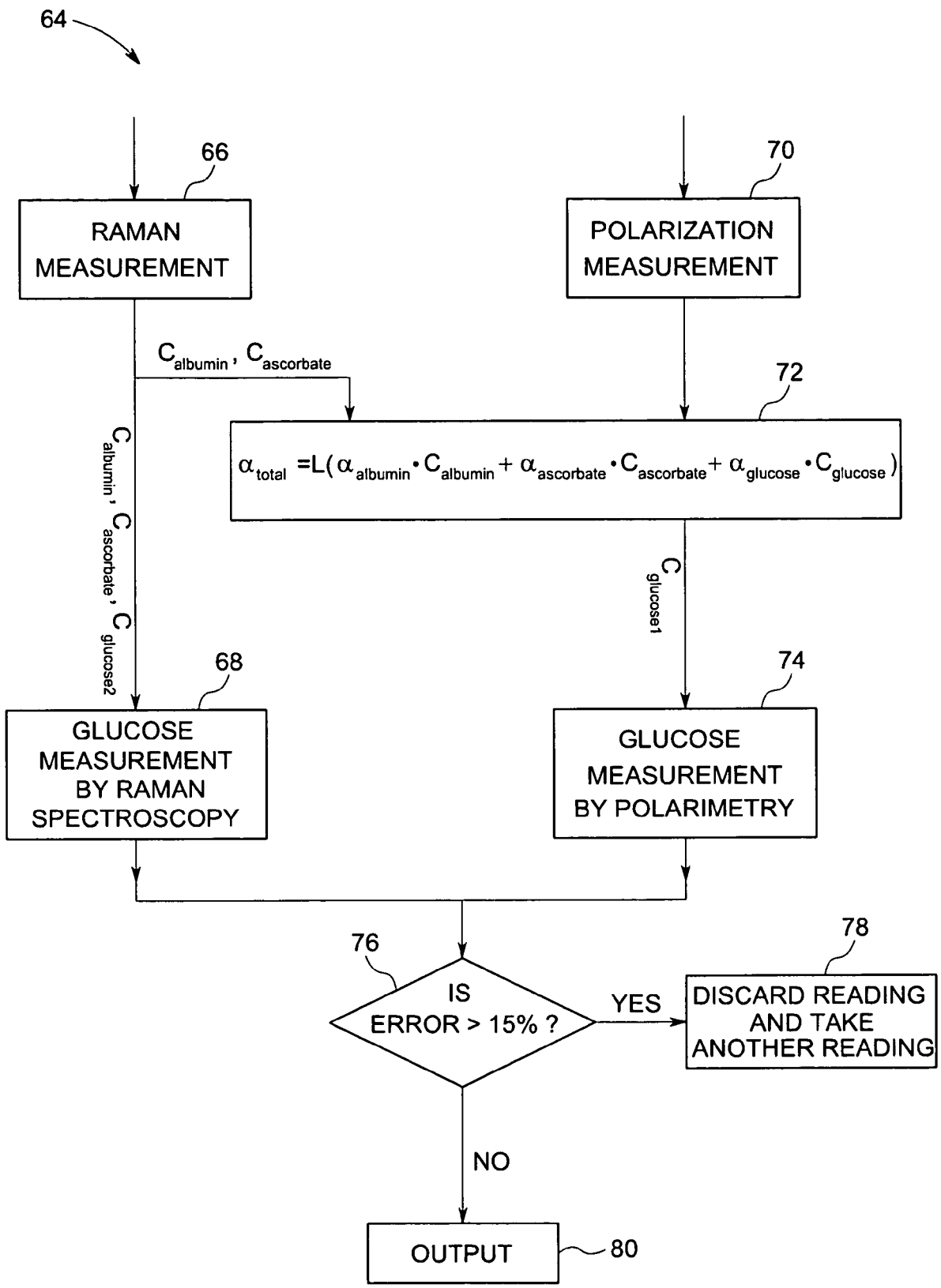
FIG. 4 is a flowchart illustrating the process of combining data acquired from a Raman spectroscopy system and a polarimetry system in accordance with an exemplary embodiment of the invention.

FIG. 4 is a flowchart 64 illustrating the process of combining data acquired from a Raman spectroscopy system and a polarimetry system in accordance with certain embodiments of the present technique. The process 64 and its various blocks may be performed by software, circuitry, hardware, and/or specific code executable by a suitable processor-based device. In the illustrated embodiment, Raman spectroscopic measurements (block 66) are acquired which provide a first analyte concentration (block 68). The first analyte concentration includes albumin concentration ($C_{albumin}$), ascorbate concentration ($C_{ascorbate}$), and glucose concentration ($C_{glucose}$). These concentration levels are measured by computing the area under the respective peak value produced by them or by analyzing the data with one of the numerous mathematical data analysis algorithms, such as principle component analysis. Similarly, polarization measurements (block 70) are acquired by the polarimetric system, which provide a second analyte concentration (blocks 72 and 74). This can be represented by the equation previously described, i.e. $a_{total} = L(a_{albumin} * C_{albumin} + a_{ascorbate} * C_{ascorbate} + a_{glucose} * C_{glucose})$. Out of the three concentration levels produced by Raman spectroscopy, $C_{albumin}$, and $C_{ascorbate}$ can be used with the above equation to solve for a glucose concentration generated by polarimetric measurement. This ensures that each of the glucose concentrations is distinctly computed. These analyte concentration levels at blocks 68 and 74 may be compared against an acceptable error limits, such as 15% for each (block 76). If error is beyond the acceptable error limit, then the reading may be discarded (block 78). However, when the measurement is within the acceptable error limit, the reading may be recorded (block 80).

The combination of polarimetric readings along with the Raman spectroscopy readings provides many advantages. The low sensitivity of Raman spectroscopy may be compensated when combined with the polarimetry readings. Further, the sensitivity of polarimetry enables measurement of rate of change of blood glucose, which facilitates continuous monitoring of blood glucose levels. Conversely, high selectivity in Raman spectroscopy may be utilized to compensate for the low selectivity of polarimetric technique. Furthermore, the robustness of Raman spectroscopy to environmental effects (e.g. temperature) compensates for the high noise levels occurring in polarimetric measurements. Moreover, combining these two techniques reduces the need for calibration.

It may be noted that the Rayleigh filter, the Raman spectrometer, and the polarimetric system may be constructed into a wearable probe, such as a pair of eyeglasses. Because these devices can be micro-machined into an integrated chip, such as a MEMS-based sensor, the MEMS-based sensor may be constructed into the wearable probe. Once the electrical signals are generated by Raman spectroscopy and polarimetry, these electrical signals may be transmitted onto a portable analysis unit, in which the computations of the analyte concentration may be performed. The portable analysis unit may be built into or separate from the probe. In embodiments in which the portable analysis unit is separate from the probe, the probe may communicate data to the analysis unit via wire or via wireless means (such as infrared, radio, optical, Bluetooth, or other signals). The portable analysis unit may include a wearable device, such as a wristwatch, or a portable device, such as a personal digital assistant (PDA), a smart phone, and the like. This implementation facilitates continuous measurement and monitoring of glucose levels. Furthermore, the analysis unit may generate alerts based on the glucose levels via a routine embedded with a processor in the analysis unit. For example, in conditions such as hypoglycemia or hyperglycemia, the portable analysis unit may generate an audible (such as an alarm or audio notification) and/or a visual alert (such as a text alert, light indication, color indication, and so forth).

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for determining analyte concentration levels, comprising:
    acquiring radiation scattered off or transmitted by a target;
    analyzing at least a first portion of the radiation via a first technique to generate a first measurement of analyte concentration levels;
    analyzing at least a second portion of the radiation via a second technique to generate a second measurement of analyte concentration levels; and
    determining analyte concentration levels based on the first measurement and the second measurement, wherein the first technique is a spectroscopic technique and the second technique is a polarimetric technique.

2. The method as recited in claim 1, wherein the first measurement of the analyte concentration levels is generated based on intensity of a shifted wavelength of a beam of photons.

3. The method as recited in claim 2, wherein the second portion of the scattered radiation comprises a portion of the beam of photons having a shift in polarization.

4. The method as recited in claim 3, wherein generating the second measurement of the analyte concentration levels comprises generating the second measurement of the analyte concentration levels based on the shift in polarization.

5. The method as recited in claim 1, wherein analyzing at least the first portion of the scattered radiation via the first technique comprises analyzing at least the first portion of the scattered radiation via Raman spectroscopy.

6. The method as recited in claim 1, comprising determining if errors in the analyte concentration levels are below predetermined estimates.

7. The method as recited in claim 1, wherein determining analyte concentration measurements comprises determining an albumin content.

8. The method as recited in claim 1, wherein determining analyte concentration measurements comprises determining an ascorbate content.

9. The method as recited in claim 1, wherein determining analyte concentration measurements comprises determining a glucose content.

10. A method for determining a glucose concentration, comprising:
    filtering radiation scattered or transmitted by an eye with an optical filter such that the radiation is separated into a first component and a second component;
    generating a first value of a glucose concentration based upon the first component with a processor; and
    generating with the processor a second value of the glucose concentration based upon the second component and the first value.

11. The method of claim 10, wherein generating the first value of the glucose concentration comprises analyzing the first component using a spectroscopic technique.

12. The method of claim 11, wherein the spectroscopic technique is a Raman spectroscopic technique.

13. The method of claim 10, wherein generating the second value of the glucose concentration comprises analyzing the second component using a polarimetric technique.

14. The method of claim 10, wherein the first component is shifted by wavelength and the second component is shifted by polarization.

15. A system for measuring an analyte concentration, comprising;
    a filter configured to separate scattered or transmitted radiation into a first portion and a second portion;
    a spectrometer configured to process the first portion to generate a first measurement of analyte concentration levels;
    a polarimeter configured to process the second portion to generate a second measurement of analyte concentration levels; and
    an analysis component configured to generate analyte concentration levels based upon the first measurement and the second measurement.

16. The system as recited in claim 15, wherein the filter comprises a Rayleigh filter.

17. The system as recited in claim 15, comprising a laser generator configured to generate the scattered or transmitted radiation.

18. The system as recited in claim 15, wherein the analysis component comprises a wearable processor-based device.

19. The system as recited in claim 15, wherein the analyte concentration level comprises glucose concentration.

20. The system as recited in claim 15, wherein the spectrometer comprises a Raman spectrometer.

21. A probe, comprising:
    a wearable filter configured to separate scattered or transmitted radiation into a first portion and a second portion;
    a wearable spectrometer configured to process the first portion and generate a first measurement;
    a wearable polarimeter configured to process the second portion and generate a second measurement; and
    a portable analysis unit configured to determine analyte concentration levels based on the first measurement and the second measurement.

* * * * *

UNITED STATES PATENT AND TRADEMARK OFFICE
CERTIFICATE OF CORRECTION

PATENT NO.       : 7,627,357 B2
APPLICATION NO. : 11/172648
DATED            : December 1, 2009
INVENTOR(S)      : Zribi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1030 days.

Signed and Sealed this

Second Day of November, 2010

David J. Kappos
*Director of the United States Patent and Trademark Office*